United States Patent [19]

Riedl et al.

[11] 4,046,015
[45] Sept. 6, 1977

[54] GLASS SAMPLING TUBE

[75] Inventors: Frederick J. Riedl, Arlington Heights; George A. Schimmelpfennig, Des Plaines, both of Ill.

[73] Assignee: UOP Inc., Des Plaines, Ill.

[21] Appl. No.: 731,500

[22] Filed: Oct. 12, 1976

[51] Int. Cl.² .......................... G01N 1/22; F17C 3/00
[52] U.S. Cl. .............................................. 73/421.5 R
[58] Field of Search ..................... 73/421, 421.5 R; 206/.6; 23/292; 215/307, 311, 313

[56] References Cited
U.S. PATENT DOCUMENTS 3,734,127  5/1973  Williams et al. .................. 23/292

*Primary Examiner*—S. Clement Swisher
*Attorney, Agent, or Firm*—James R. Hoatson, Jr.; Barry L. Clark; William H. Page, II

[57] ABSTRACT

Glass sampling tube for collecting and storing gas samples has tapered ground glass joints at either end of a tubular storage chamber for permitting selective communication between axially extending inlet tube portions on the ends of the device and the storage chamber. The joints are protected against breakage by being entirely within the tubular storage chamber but include manually actuable external handle portions which are positioned integrally with and intermediate the inlet tube portions and the joints.

8 Claims, 4 Drawing Figures

GLASS SAMPLING TUBE

BACKGROUND OF THE INVENTION

The invention relates to glass sample containers of the type used in collecting and storing samples of a gas to be analyzed at a future time. Typically, such samplers comprise a cylindrical central tube portion which is necked down at each end and attached to the side of a tapered ground glass joint member which has a transverse opening permitting selective communication between the end of the central tube portion and an inlet tube portion fastened to the joint member on the side thereof which is opposite to the central tube portion. The aforementioned containers are very expensive to make and are very easily broken, either due to the joints (which often extend radially beyond the central tube) being broken off as the units are moved into or out of storage compartments or due to the joints being broken off as the central joint member is rotated while holding the central tube. One configuration proposed in an attempt to solve the breakage problem utilizes an inlet tube as a sealing plunger and includes an O-ring around the inlet tube for sealing. This latter device has not worked well and many gas samples have been lost through leakage.

SUMMARY

It is among the objects of the present invention to provide a gas sampling tube which will provide the positive sealing action of a ground glass joint while avoiding the breakage problems presented by the prior art devices. These and other objects are attained by the present invention wherein ground and tapered glass joint members are inserted within the ends of the sampling tube so that transverse flanges on the outer end of the female portion of the joint are integrally welded to the sampling tube. An axial inlet tube is welded to the outer end of the inner or male portion of the joint and a pair of handles or ears are also formed on the sides of the inlet tube adjacent the end of the sampling tube to permit manual actuation of the valve formed by the joint. The ears also form retaining members at opposite ends of the sampling tube between which a rubber band or other type of resilient member may be positioned so as to bias the joints into tight sealing engagement.

An internal tube or passageway is formed inside the inner joint member to carry fluid between the inlet tube and the interior of the sampling tube. The internal tube terminates at an opening in the side wall of the male joint member. An opening through the side wall of the outer or female joint member can be selectively aligned with the opening in the side wall of the inner joint member to permit flow by turning the handles to rotate the inner member. When the openings are not aligned, the joint is sealed, with the seal being enhanced by a coating of grease.

DESCRIPTION OF THE PREFERRED EMBODIMENT

Figure 1:
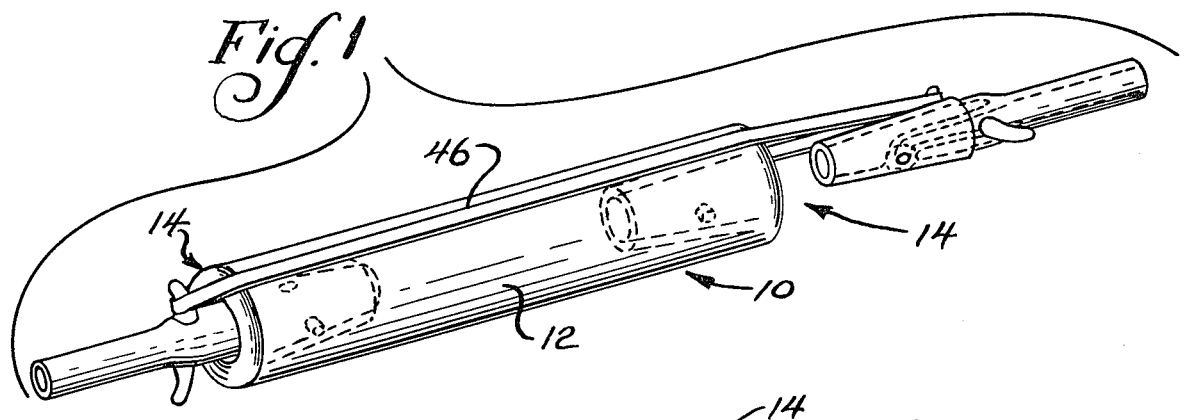
FIG. 1 is a perspective view of the improved sample tube with one end joint being exploded outwardly for clarity.

Referring to FIG. 1, the improved glass sampling apparatus indicated generally at 10 includes a central tube portion 12 having joint portions 14 at each end thereof. The tube portion 12 may have varying diameters and lengths depending upon the volumetric capacity desired. Each of the joint portions 14 comprises a tapered outer or female portion 16 having a radially outwardly extending flange portion 18 at its outer end which is sealed or welded at 20 to the central tube portion 12. The movable portion of the joint 14 comprises a tapered inner or male portion 22 which has a ground outer sealing wall 24 which is adapted to sealingly engage a ground inner wall 26 on the inner portion 16. Although not shown, the quality of the seal is generally enhanced by applying a thin coating of a suitable stopcock grease to the wall 24. An inlet tube 30 is welded at 32 to the inner member 22 and, as seen more clearly in FIG. 2, an internal tube 34 is welded at 36 to the inlet tube 30. The internal tube 34 is also welded at 38 to the wall of the inner member 22 in communication with an opening 40 formed in said wall. The opening 40 in the inner member is designed to be selectively engaged with opening 41 in the outer member 16 so that a fluid entering or leaving tube 30, usually by means of a rubber tube (not shown), can be carried into the apparatus 10. To facilitate manual rotation of the inner member 22 a pair of ears 42 are welded thereon. Preferably, the ears 42 are formed so as to provide retaining portions 44 which may be engaged by a rubber band 46 or other suitable resilient member which will hold the portions of the joint in mating engagement.

Figure 2:
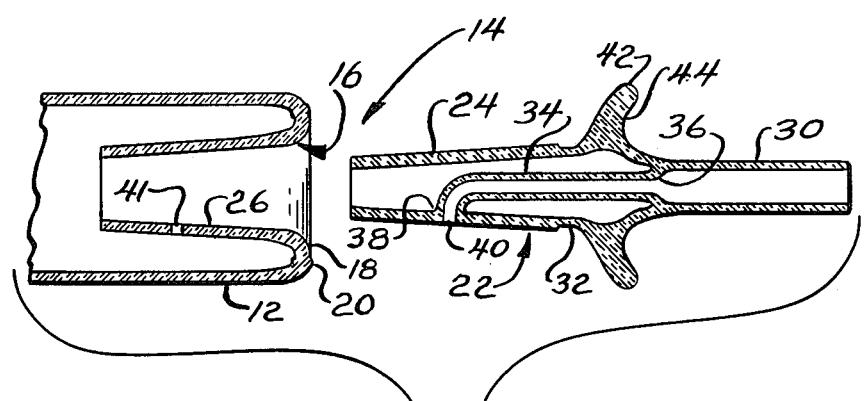
FIG. 2 is a fragmentary axial section view of the right end of the assembly shown in FIG. 1.
Figure 3:
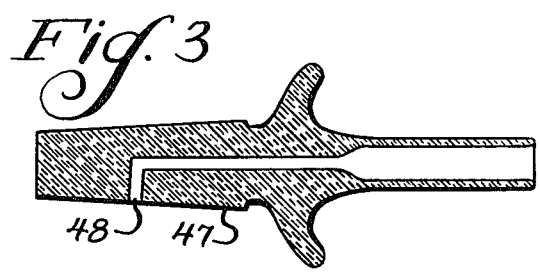
FIG. 3 is a side sectional view of an alternative form of inner joint member.

Referring to FIG. 3, a slightly modified form of inner joint is shown which includes a passageway 48 drilled or otherwise formed in the end of a solid outer member 47 in place of the internal tube 34 shown in FIG. 2.

Figure 4:
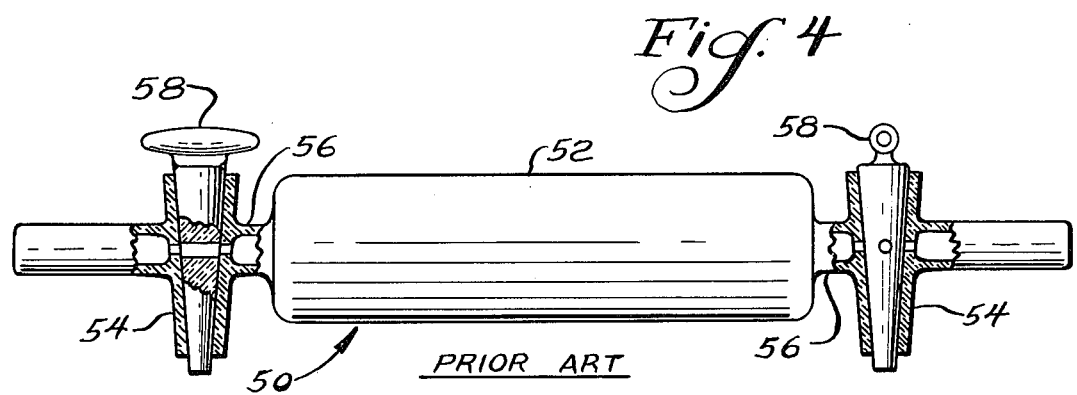
FIG. 4 is a side sectional view of a prior art sampling tube.

A prior art glass sampling apparatus indicated generally at 50 is shown in FIG. 4. The apparatus 50 includes a tubular center portion 52 and joint portions 54 connected to the tube portion by necked down joining portions 56. As previously mentioned, the design is quite fragile since the joint portions 54 can be easily broken off through careless handling or by a user applying excessive force to one of the actuating handles 58 with one hand while holding the tube portion 52 with the other.

We claim as our invention:

1. In a glass gas sampling tube comprising a tubular body portion having an axially positioned inlet tube portion at each end and sealable joint means at each end for selectively sealing said inlet tubes from the interior of said body portion, the improvement comprising said joint means being formed of axially extending tapered male inner and female outer glass wall portions which are positioned in cooperating relationship within the body portion and radially spaced from the walls of said body portion, said inner portion having a first opening in its wall portion in open communication with said inlet tube portion, said outer portion having a second opening in its wall portion, and manually actuated handle portions integral with said inner portion for selectively rotating said inner portion in said outer portion for moving said first opening into or out of communication with said second opening.

2. The sampling tube of claim 1 wherein said inner and outer wall portions of said joint means are ground in at least their areas of cooperating contact with each other.

3. The sampling tube of claim 2 wherein said inner and outer wall portions which are ground have a grease sealing film applied to them.

4. The sampling tube of claim 2 wherein said inner portions are resiliently biased toward each other and into engagement with said outer portions.

5. The sampling tube of claim 4 wherein said inner portions are biased by a rubber band.

6. The sampling tube of claim 5 wherein said handle portions extend radially and axially outwardly so as to form a retaining means for said rubber band.

7. The sampling tube of claim 2 wherein said inner portion is hollow except for a tubular portion extending between said first opening and said inlet tube.

8. The sampling tube of claim 2 wherein said inner portion is solid except for an open passageway between said first opening and said inlet tube.

* * * * *